United States Patent [19]

Osborne et al.

[11] Patent Number: 5,119,827
[45] Date of Patent: Jun. 9, 1992

[54] MECHANISMS OF ANTIESTROGEN RESISTANCE IN BREAST CANCER

[75] Inventors: C. Kent Osborne, San Antonio, Tex.; Michael W. De Gregorio, Hamden, Conn.

[73] Assignees: Board of Regents, The University of Texas System, Austin, Tex.; Yale University, New Haven, Conn.

[21] Appl. No.: 577,790

[22] Filed: Sep. 5, 1990

[51] Int. Cl.$^5$ .............................................. A61B 10/00
[52] U.S. Cl. ................................... 128/749; 128/898; 436/64; 435/4; 435/32; 424/9
[58] Field of Search ................................. 604/48–50, 604/51; 128/749, 898; 436/64; 435/4, 32; 424/9

[56] References Cited

U.S. PATENT DOCUMENTS

| 4,806,464 | 2/1991 | Spelsberg | 435/6 |
| 4,919,937 | 4/1990 | Mauvais-Jarvis et al. | 424/449 |
| 5,023,234 | 6/1991 | Labrie | 514/15 |
| 5,030,417 | 7/1991 | Spelsberg | 422/61 |

FOREIGN PATENT DOCUMENTS

| 0272791 | 6/1988 | European Pat. Off. | 435/32 |
| 8901153 | 2/1989 | World Int. Prop. O. | 436/64 |

OTHER PUBLICATIONS

CA114(7):55296d, Structure-Function Relationships of Hydroxylated Metabolites of Tamoxifen that Control the Proliferation of Estrogen-Responsive T47D Breast Cancer Cells In Vitro, Murphy et al., 1990.
CA108(23):198501d Ligand Interaction of the Estrogen Receptor to Program Antiestrogen Action: A Study With Non-Steroidal Compounds In-Vitro, Craig et al., 1988.
W. E. Simon et al., "Development of Resistance to Tamoxifen and Progestins in Human Mammary Cancer", Proc. Int. Congr. Chemother., 13th, vol. 18, 270/1-270/4, 1983.
Jordan, et al., Endocrinology, 122(4):1449-1454, 1988, "Ligand Interaction at the Estrogen Receptor to Program Antiestrogen Action: A Study With Nonsteroidal Compounds in Vitro".
Armstrong et al., J. Chromat., 414:192–96, 1987, "Separation of Tamoxifen Geometric Isomers and Metabolites by Bonded-Phase β-Cyclodextrin Chromatography".
Katzenellenbogen et al., J. Steroid Biochem., 22(5):589-96, 1985, "Facile Geometric Isomerization of Phenolic Non-Steroidal Estrogens and Antiestrogens: Limitations to the Interpretation of Experiments Characterizing the Activity of Individual Isomers".
Katzenellenbogen et al., Cancer Res., 44:112-19, 1984, "Bioactivities, Estrogen Receptor Interactions, and Plasminogen Activator-Inducing Activities of Tamoxifen and Hydroxy-Tamoxifen Isomers in MCF-7 Human Breast Cancer Cells".
Robertson et al., J. Steroid Biochem., 16:1-13, 1982, "Tamoxifen Antiestrogens, a Comparison of the Activity, Pharmacokinetics, and Metabolic Activation of the Cis and Trans Isomers of Tamoxifen".

(List continued on next page.)

Primary Examiner—C. Fred Rosenbaum
Assistant Examiner—Mark O. Polutta
Attorney, Agent, or Firm—Arnold, White & Durkee

[57] ABSTRACT

The present invention involves a method for early detection of developing tamoxifen resistance in breast cancer. Tamoxifen is the drug of choice for hormonal therapy of a first recurrence of breast cancer, but its use is always associated eventually with emergence of resistant tumors. Whereas initial treatment is usually followed by tumor regression, resistant tumors may actually resume growth under continued tamoxifen treatment. Because such growth may actually be augmented by the tamoxifen, it is essential to identify the onset of resistance as early as possible so alternative therapy may be promptly instituted.

14 Claims, 7 Drawing Sheets

OTHER PUBLICATIONS

Jordan et al., *Endocrinology*, 108(4):1353-61, 1981, "Geometric Isomers of Substituted Triphenylethylenes and Antiestrogen Action".

Jordan et al., *Cancer Treatment Reports*, 60(10):1409-19, 1976, "Antiestrogenic and Antitumor Properties of Tamoxifen in Laboratory Animals".

Fromson et al., *Xenobiotica*, 3(11):711-14, 1973, "The Metabolism of Tamoxifen (I.C.I. 46,474) Part II: in Female Patients".

Fromson et al., *Xenobiotica*, 3(11):693-704, 1973, "The Metabolism of Tamoxifen (I.C.I. 46,474) Part I: in Laboratory Animals".

Terenius, *Acta Endocrinologica*, 66:431-47, 1971, "Structure-Activity Relationships of Anti-Oestrogens with Regard to Interaction with 17$\beta$-Oestradiol in the Mouse Uterus and Vagina".

Harper et al., *J. Reprod. Fert.*, 13:101-119, 1967, "A New Derivative of Triphenylethylene: Effect on Implantation and Mode of Action in Rats".

MECHANISMS OF ANTIESTROGEN RESISTANCE IN BREAST CANCER

BACKGROUND OF THE INVENTION

The present invention relates to methods for monitoring the effectiveness of tamoxifen (2-[4-(1,2-diphenyl-1-butenyl)phenoxy]-N,N-dimethylethanamine) therapy in the treatment of breast cancer, and more particularly to methods of detecting the emergence of tamoxifen-resistant tumors and the resulting treatment resistance by means of an analytical assay for antiestrogenic and other forms of tamoxifen and its metabolites.

Breast cancer is the most common form of malignant disease among women of the Western world, and it is the most common cause of death among those between 40 and 45 years of age. This disease will develop in about six to seven percent of women in the United States, and at the present time about one half of this group can be cured. The treatment of breast cancer involves surgery, radiation, chemotherapeutics and hormonal therapy, the last category including consideration of antiestrogens for treatment of endocrine-responsive tumors.

Tumors sensitive to estrogen stimulation may regress following competitive inhibition of estrogen receptors by tamoxifen (an antiestrogen), and response is currently predicted based on the stage of disease and on the basis of assays for estrogen receptors (ER) and progesterone receptors (PR) in the tissue. Many breast cancers and all normal estrogen-responsive tissues contain these labile cytoplasmic proteins which bind estrogen and progesterone. Patients with positive assays for these proteins have an objective response to hormone therapy of about 65%, while those with negative assays have an objective response rate of <10%. For postmenopausal women having a first recurrence of breast cancer with an ER+ or PR+ assay, tamoxifen therapy is the treatment of choice.

Notwithstanding strong interest in the use of antiestrogens in breast cancer treatment, however, incomplete knowledge of their basic pharmacology persists. Substituted triphenylethylenes (including tamoxifen) have antiestrogen effects which appear to be dependent on geometric isomerism. For example, trans-tamoxifen (the isomer used in tamoxifen therapy) is an antiestrogen, whereas the cis isomer is a weak estrogen. The present invention makes use of newly acquired knowledge about in vivo interconversion of geometric isomers to improve treatment of breast cancer.

Although tamoxifen is the most widely used antiestrogen for treating breast cancer, development of tamoxifen resistance and subsequent tumor progression during tamoxifen therapy represents a major reason for treatment failures. The mechanism of tamoxifen resistance has been unknown, but an estrogenic metabolite of tamoxifen which would promote growth in ER+ tamoxifen-resistant tumors has been identified.

SUMMARY OF THE INVENTION

The present invention relates to the use of tamoxifen metabolites as early indicators of tamoxifen resistance (prior to clinical treatment failure). Tamoxifen is representative of a group of compounds called triphenylethylene antiestrogens, whose effect is to slow or stop the growth of estrogen-dependent tumors. While it is the most commonly used drug for treatment of breast cancer today, tamoxifen is associated with the development of drug resistance in virtually all patients who take it. With the onset of resistance, tumor growth resumes or accelerates and tamoxifen therapy should be discontinued. Renewed tumor growth will eventually become obvious, of course, but an objective of the present invention is to provide early warning of tamoxifen resistance so that therapy can be changed promptly as needed.

The mechanism of tamoxifen resistance is unknown, but it is known that tamoxifen exists as two geometric isomers, the trans form (an antiestrogen) and the cis form (a weak estrogen). The trans form, of course, is the therapeutic drug for breast cancer. Further, however, it has been shown that there can be interconversion from one isomer to the other in tissue culture cells and also, presumably, in patients (though this has not been demonstrated).

The model with which the present invention was developed consists of human breast cancer cells growing subcutaneously in athymic nude mice. Treatment of the mice with tamoxifen results in tumor growth inhibition for four to six months, followed by the onset of tumor resistance and regrowth (much as in humans). Further, tumor regrowth is actually stimulated by tamoxifen. Even when transplanted into different mice, the resistant tumors will not grow unless stimulated by tamoxifen or estrogen. Tamoxifen, in these cases, appears to mimic the action of estrogen.

One of the possible mechanisms for development of tamoxifen resistance is hypothesized to be conversion over time of both tamoxifen and its metabolites from trans (antiestrogen) forms to cis forms which have estrogen-like activity. Assays for the presence of both trans and cis forms can be accomplished with a high performance liquid chromatography (HPLC) system. In three separate blinded experiments using such a system, it has been shown that:

1) tumors from tamoxifen-resistant mice have significantly lower concentrations of tamoxifen than sensitive tumors (whose growth is still arrested); and
2) there is an increase in the cis-4-hydroxytamoxifen/trans-4-hydroxytamoxifen (C/T-OH-TAM) ratio in resistant tumors.

Actual values of the C/T-OH-TAM ratio are about 0.4–0.5 in sensitive tumors and 0.8–0.9 in resistant tumors. While it can not be confirmed that the increased estrogen effect resulting from an elevated C/T-OH-TAM ratio is the reason for development of resistance, the association appears to be consistent.

DESCRIPTION OF THE PREFERRED EMBODIMENTS

Those skilled in the art will recognize that changes analogous to those detected in the C/T-OH-TAM ratio might occur in cis-tamoxifen or other (monophenol and bisphenol) tamoxifen metabolites or in any of the triphenylethylene antiestrogens related to tamoxifen. Nevertheless, the best mode of implementing the present invention now appears to be in conjunction with treatment of estrogen-responsive breast cancer with tamoxifen and detection of the onset of tamoxifen resistance.

Those skilled in the art will also recognize that if geometric isomerization or metabolism to other estrogenic metabolites proves to be the mechanism of antiestrogen resistance, synthesis of antiestrogens which preclude isomerization may be a fruitful path to improved treatment. At the present time, however, tamoxifen is the drug of choice for hormonal treatment of recurrent breast cancer, and its invariable association with the onset of tumor resistance and tamoxifen-enhanced tumor growth makes the present invention a valuable aid to therapy.

Claims are directed to the two main indicators which have been discovered to be closely associated with the onset of tumor tamoxifen resistance. Elevation of the C/T ratio for 4-OH-TAM in tumor or blood, and depression of the tamoxifen concentration in tumor are both shown by experimental data to be useful predictors of recrudescence of tumor growth despite (and perhaps in-part because of) tamoxifen treatment. Either indicator can be used alone, or they may be used together.

For each indicator, small changes (about a few percent) in the direction indicated by this specification and claims are believed to indicate the early stages of tumor resistance. Larger indicator changes (up to about 80 to 100 percent) can be expected when tumor resistance is well established. Examples of in vitro and in vivo tests are provided to illustrate the specific utility of the claimed invention and to support both the approximate magnitude of indicator changes and the extrapolations suggested in this specification.

These examples are presented to describe preferred embodiments and utilities of the present invention and are not meant to limit the present invention unless otherwise stated in the claims appended hereto. Taken together, the examples illustrate the best mode of implementing the invention as it is currently understood.

EXAMPLE 1

Mouse MCF-7 Tumor Model

In order to examine the relationship between tamoxifen metabolites and tamoxifen resistance, athymic Balb/c nude mice were implanted with human breast cancer tumor cells (MCF-7). Mice were treated daily for 4–6 months with subcutaneous tamoxifen. After tamoxifen resistance developed and tumor progression was observed, mice were sacrificed, and tumors were collected. In addition, tamoxifen-sensitive tumors were collected from mice still responding to tamoxifen therapy.

Analytical Methodology

Quantification of tamoxifen and its metabolites in tumor specimens was performed using photactivation and high performance liquid chromatography (HPLC) analysis. To summarize: Each tumor sample was weighed, spiked with an internal standard, and homogenized. Tissue samples were then extracted with 2% n-butanol in hexane and irradiated with high intensity ultraviolet light (254 nm). Samples were analyzed by HPLC using a C-18 reverse phase column and eluted isocratically with a mobile phase of water (7%) and triethylamine (0.25%) in methanol. All solvents were of HPLC grade. Fluorescence of all compounds was measured at a wavelength of 266 nm. The sensitivity of this assay was approximately 2 ngs/gm for trans-tamoxifen, n-desmethyltamoxifen and cis and trans-4-hydroxytamoxifen. Linerarity was measured through a concentration range of 25–3,000 ngs for all compounds, with a correlation coefficient of greater than 0.993. Cis and trans-4-hydroxytamoxifen ratios were calculated based on peak-heights. In some samples, the tumor was first homogenized and then the nuclear pellet obtained by centrifugation. HPLC tamoxifen measurements were made on extracts of the entire tumor specimen or on subcellular fractions including the cytosol or the total nuclear pellet. In some cases, the nuclear pellet was further extracted in 0.4M KCl to extract primary metabolites bound to estrogen receptor.

Chromatographs (Mouse Studies)

Figure 1:
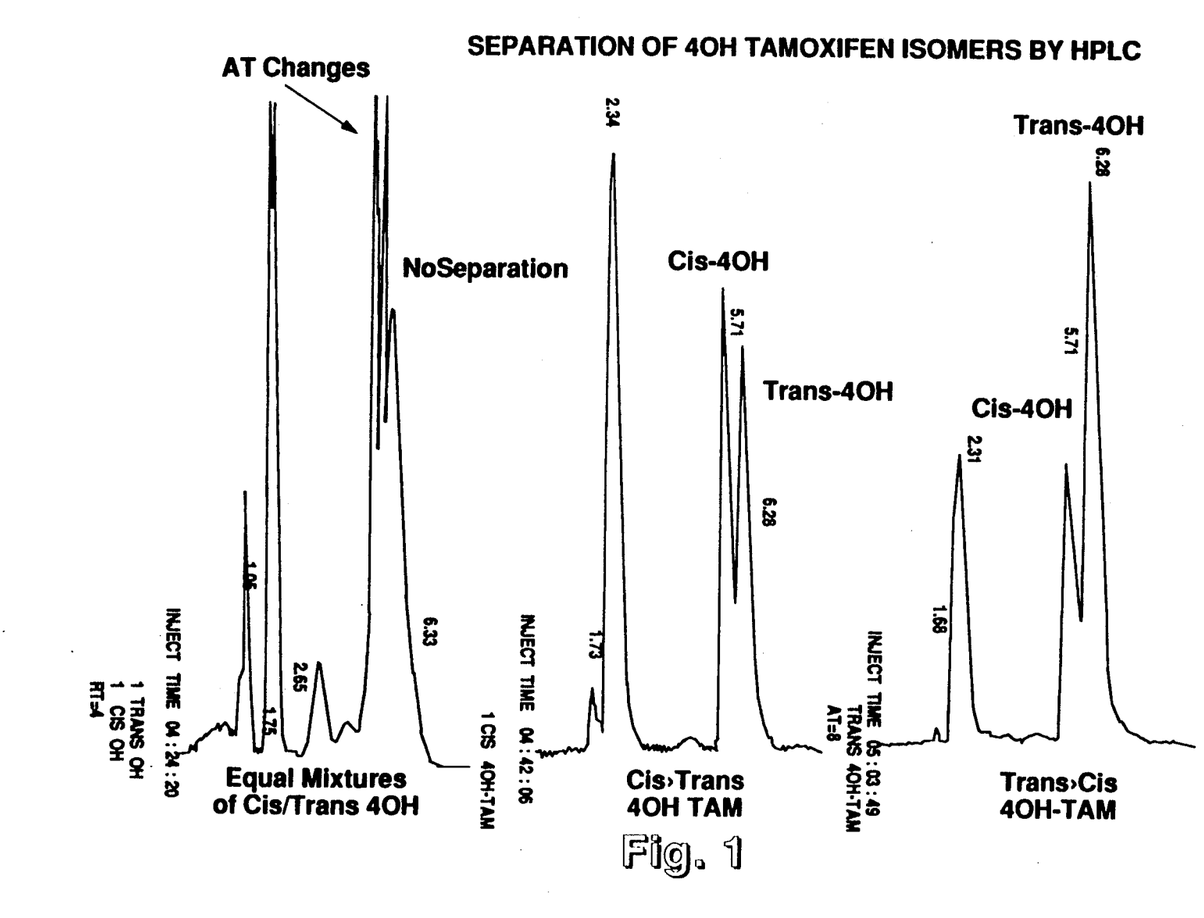
FIG. 1 shows HPLC tracings of 400 ng/ml stock solutions of trans and cis 4-hydroxytamoxifen (4-OH-TAM), respectively.

FIG. 1 shows HPLC tracings of 400 ng/ml stock solutions of trans and cis 4-OH-TAM isomers mixed so as to yield a solution with equal amounts of the isomers, as well as a solution in which the trans isomer predominated and one in which the cis isomer predominated. These tracings suggest that specimens may be analyzed to indicate relative amounts of the geometric isomers present, thus providing a means of easily following a patient's response to tamoxifen therapy using the present invention.

Figure 2:
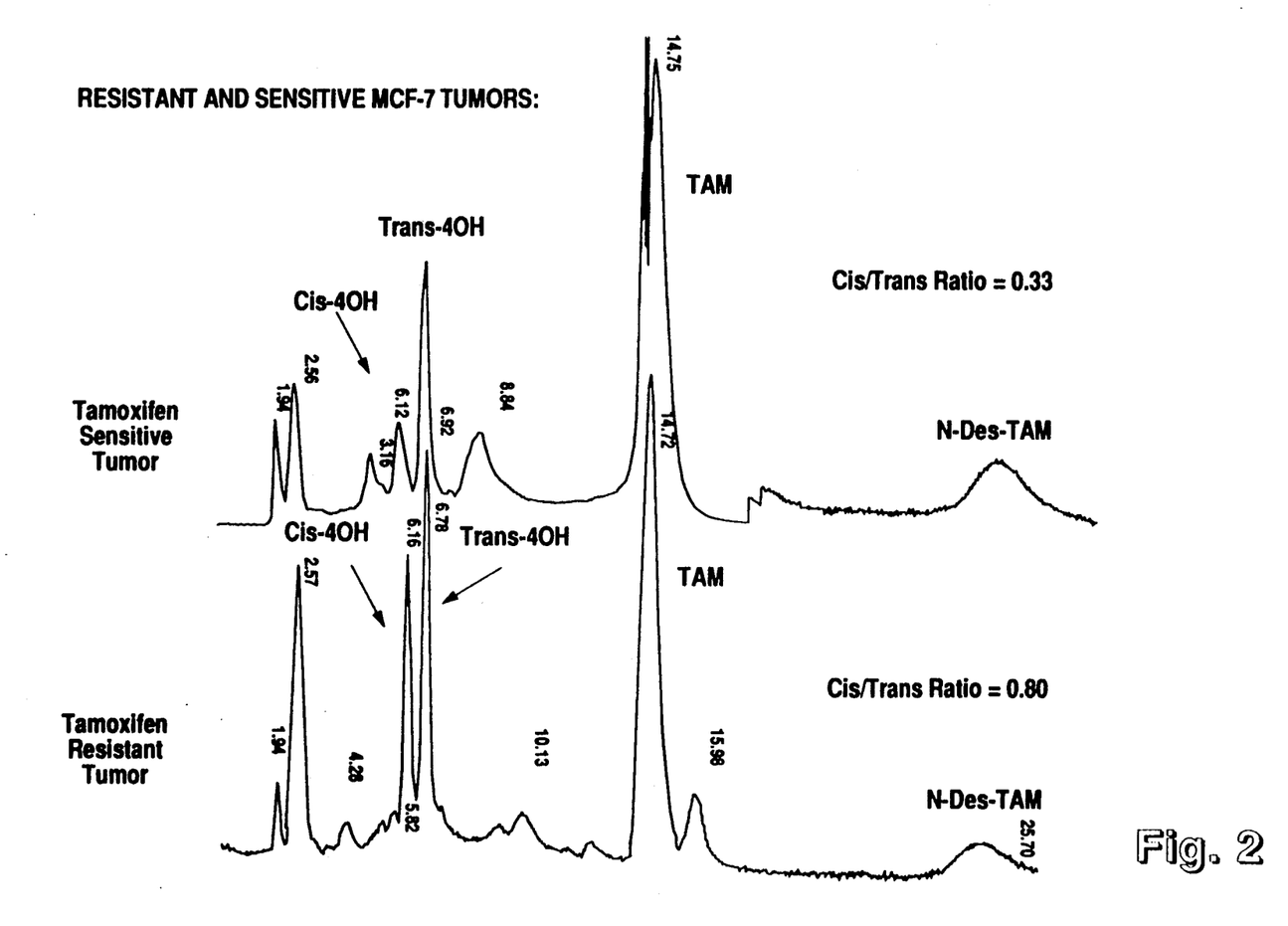
FIG. 2 shows HPLC chromatographs indicating that the cis/trans ratio of 4-OH-TAM is lower in sensitive than in resistant tumors isolated from athymic nude mice.

FIG. 2 shows HPLC tracings indicating relative amounts of trans and cis 4-OH-TAM in sensitive and resistant tumors isolated from tamoxifen-treated athymic nude mice. These figures demonstrate identification of cis and trans 4-OH-TAM in tamoxifen-resistant and sensitive tumors. Further, they demonstrate that the cis/trans ratio is higher in the resistant tumor.

Figure 3:
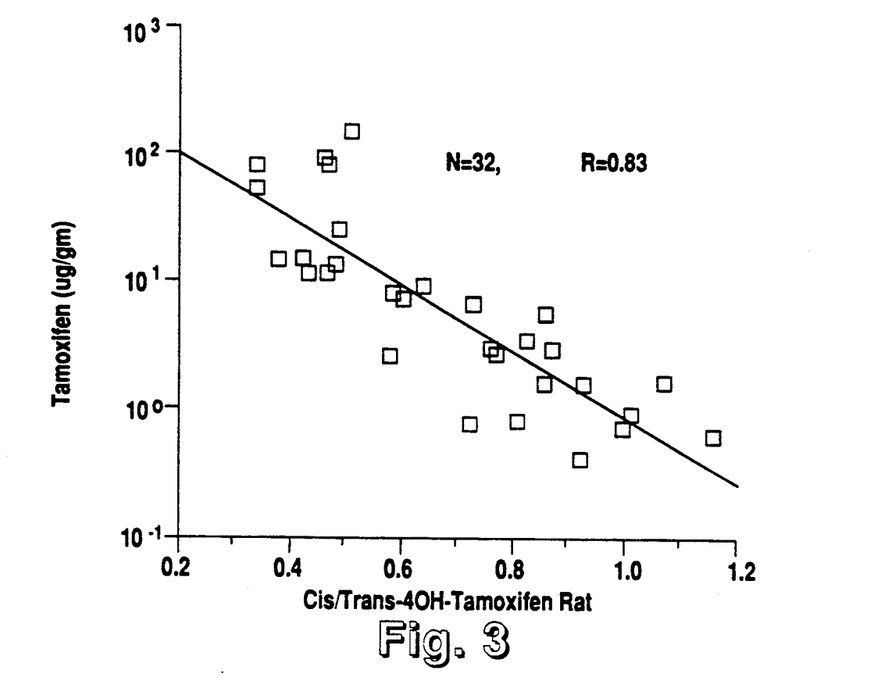
FIG. 3 shows the approximately linear inverse relationship which exists between the logarithm of total tumor tamoxifen concentration and the cis/trans 4-OH-TAM ratio (N=32, R=0.83, linear regression analysis).

FIG. 3 shows the approximately linear inverse relationship of the logarithm of total tumor tamoxifen concentration to cis/trans 4-OH-TAM ratios (N =32, R =0.83, linear regression analysis). This graph suggests that because total tumor tamoxifen concentration is related to the geometric isomer ratio, only one of these quantities may be needed to predict emergence of tumor resistance. Because determination of the isomer ratio does not require absolute concentrations, it may be a more convenient measure for clinical evaluation of tamoxifen-treated patients.

Figure 4:
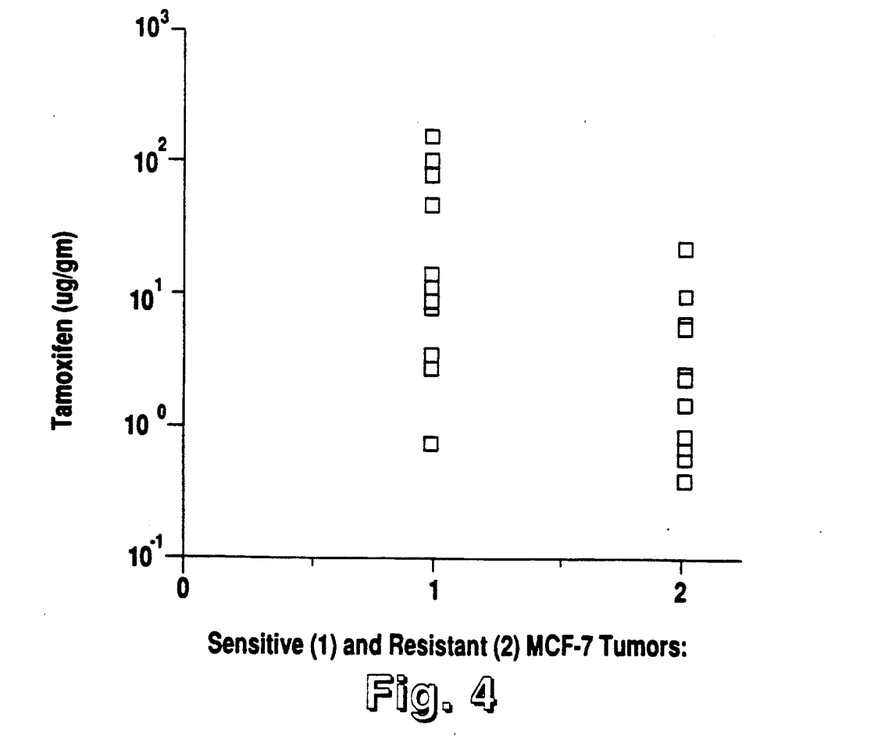
FIG. 4 shows a scatter plot of tamoxifen concentrations in sensitive and resistant MCF-7 tumors (N=32).

FIG. 4 shows a scatter plot of tamoxifen concentrations in sensitive and resistant MCF-7 tumors (N =32). Mean tamoxifen concentrations in sensitive tumors is 36 ug/gm (SD =46.41), versus 4.38 ug/gm in resistant MCF-7 tumors (SD=6.22). These differences are highly statistically significant (P <0.0005) by the Wilcoxon Rank Sum test. See Table 1 for Data.

The median tamixifen concentration in sensitive tumors is 12.475 ug/gm and in resistant tumors it is 2.2 ug/gm. 10 of 16

The median tamoxifen concentration in sensitive tumors is 12.475 ug/gm and in resistant tumors it is 2.2 ug/gm. 10 of 16 sensitive tumors had values greater than 10 ug/gm compared to only 2 of 16 resistant tumors. This graph implies that while individual tamoxifen concentrations might not be determinative of tamoxifen resistance, a trench in such numbers of a particular patient could be helpful in making therapeutic decisions.

TABLE 1

Tamoxifen Concentrations in Sensitive and Resistant MCF-7 tumors.

| | Tamoxifen (ug/gm) | |
|---|---|---|
| | Sensitive (N = 16) | Resistant (N = 16) |
| 1. | 101.55 | 1.82 |
| 2. | 84.47 | 25.12 |
| 3. | 10.76 | 6.93 |
| 4. | 159.24 | 3.3 |
| 5. | 80.94 | 2.58 |
| 6. | 12.69 | 6.08 |
| 7. | 50.7 | 0.745 |
| 8. | 15.36 | 0.688 |
| 9. | 0.766 | 3.348 |
| 10. | 2.78 | 0.45 |
| 11. | 8.85 | 1.64 |
| 12. | 8.08 | 0.814 |
| 13. | 12.26 | 11.12 |
| 14. | 9.45 | 1.66 |
| 15. | 14.4 | 2.81 |
| 16. | 3.79 | 0.981 |
| Mean | 36 ug/gm | 4.38 ug/gm |
| | $p < 0.0005$ | |
| | SD = 46.41 ug/gm | SD = 6.22 ug/gm |
| | Range = 0.77–159.24 | Range = 0.45–25.12 |
| | 10/16 are > 10 ug/gm | 2/16 > 10 ug/gm |
| | median = 12.475 ug/gm | median = 2.2 ug/gm |

Figure 5:
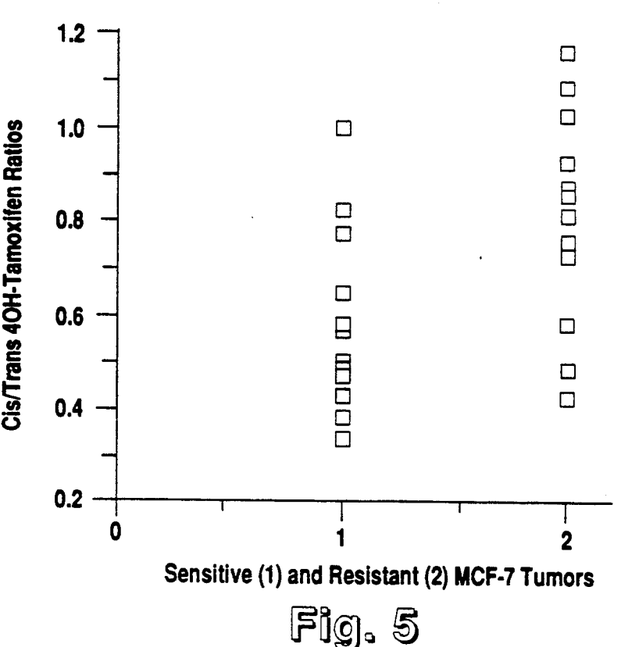
FIG. 5 shows a scatter plot of 4-OH-TAM ratios (cis/trans) in sensitive and resistant MCF-7 tumors (N=32).

FIG. 5 shows a scatter plot of cis/trans 4-OH-TAM ratios in sensitive and resistant MCF-7 tumors (N=32). The means 4-0.8141 (SD=0.196). These differences are again highly statistically significant (P<0.0005). See Table 2 for cis/trans 4-OH-TAM data.

By reasoning similar to that for FIG. 4, this graph implies that while individual cis/trans ratio determinations might not be determinative of tamoxifen resistance, a trend in such numbers for a particular patient could be helpful in making therapeutic decisions.

TABLE 2

Cis/trans 4-OH-TAM ratios in sensitive and resistant MCF-7 tumors.

| | Cis/Trans 4OH-Tamoxifen | |
|---|---|---|
| | Sensitive (N = 16) | Resistant (N = 16) |
| 1. | 0.575 | 0.86 |
| 2. | 0.588 | 0.812 |
| 3. | 0.472 | 0.442 |
| 4. | 0.56 | 0.929 |
| 5. | 0.645 | 1.019 |
| 6. | 0.428 | 0.777 |
| 7. | 0.446 | 1.073 |
| 8. | 0.4632 | 0.49 |
| 9. | 0.476 | 0.724 |
| 10. | 0.506 | 0.868 |
| 11. | 0.34 | 0.59 |
| 12. | 0.486 | 0.86 |
| 13. | 0.34 | 0.73 |
| 14. | 0.38 | 1.16 |
| 15. | 1.0 | 0.76 |
| 16. | 0.77 | 0.932 |
| Mean | 0.5297 | 0.8141 |
| | $p < 0.0005$ | |
| | SD = 0.168 | SD = 0.196 |
| | Range = (0.34–1.0) | Range = (0.442–1.16) |
| | Median = 0.48 | Median = 0.84 |
| | 3/16 > 0.06 | 3.16 ≦ 0.60 |
| | 13/16 ≦ 0.60 | 13/16 > 0.60 |

Figure 6:
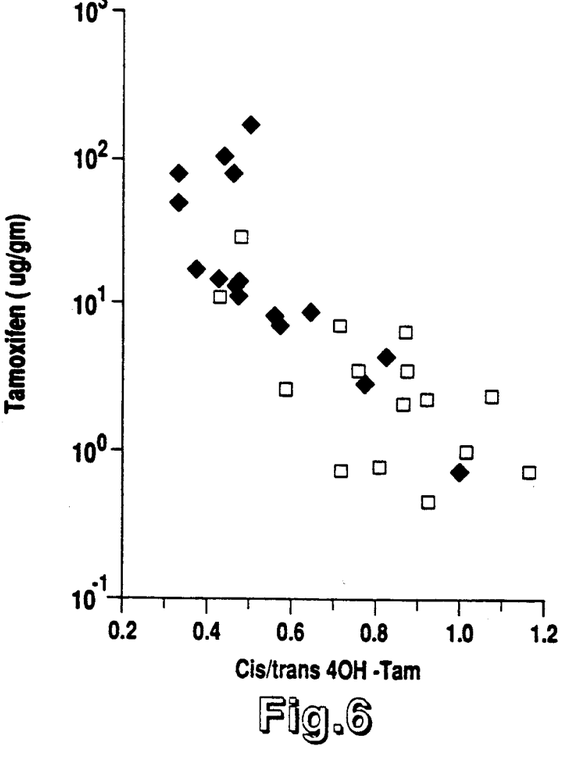
FIG. 6 shows a scatter plot of tamoxifen versus cis-/trans 4-OH-TAM ratios in resistant (open symbols) and sensitive (solid symbols) tumors.

FIG. 6 shows the scatter plot of FIG. 3 except for removal of the regression line and addition of identification for resistant (open symbols) and sensitive (solid symbols) tumors. This scatter plot demonstrates the relationship among cis/trans rations, total tumor tamoxifen concentration, and tamoxifen resistance. Resistant tumors tend to have lower tamoxifen concentrations and higher cis/trans ratios. Nevertheless, this graph like FIGS. 3, 4, and 5 suggests that trend data will be more useful in therapeutic decisions for a given patient than single determinations of either tamoxifen concentration or the cis/trans ratio.

Table 3 shows cis/trans ratios and tamoxifen concentrations in nuclear extractions versus nuclear pellets extracted with 0.4 molar KCl followed by 200,000 G centrifugation at 4°. The material extracted with KCl includes that bound to estrogen receptor. The results of this experiment suggest that tamoxifensensitive tumors generally have a higher percentage of the major antiestrogen metabolite, trans 4-OH-TAM. In addition, tamoxifen resistant tumors generally have reduced tamoxifen concentrations, together with high levels of the less antiestrogenic and more estrogenic metabolite cis 4-OH-TAM. Therefore, levels of geometric isomers of the 4-OH-TAM metabolite, together with tamoxifen levels, may indicate tumor sensitivity.

TABLE 3

Study #4 Tumors 2 to 13
Cis/Trans Ratios - Tamoxifen Levels - R/S

| tumor # | cis/trans ratio | tamoxifen level (conc/g) | S/R |
|---|---|---|---|
| 2 Total Nuclear | 0.6846 | 3,440.28 | sensitive |
| 2 KCl Nuclear Extract | trans only | 664.26 | |
| 3 Total Nuclear | 1.0455 | 2,568.63 | sensitive |
| 3 KCl Nuclear Extract | — | 825.35 | |
| 4 Total Nuclear | 0.4620 | — | resistant |
| 4 KCl Nuclear Extract | 0.9195 | 798.48 | |
| 5 Total Nuclear | 0.6632 | 4,282.17 | sensitive |
| 5 KCl Nuclear Extract | trans only | 412.68 | |
| 6 Total Nuclear | 1.0209 | 796.78 | resistant |
| 6 KCl Nuclear Extract | 1.9248 | 157.96 | |
| 7 Total Nuclear | 0.9401 | 713.43 | resistant |
| 7 KCl Nuclear Extract | 1.3808 | 148.67 | |
| 8 Total Nuclear | 1.0059 | 1,891.92 | sensitive |

TABLE 3-continued

Study #4 Tumors 2 to 13
Cis/Trans Ratios - Tamoxifen Levels - R/S

| tumor # | cis/trans ratio | tamoxifen level (conc/g) | S/R |
|---|---|---|---|
| 8 KCl Nuclear Extract | — | 454.25 | |
| 9 Total Nuclear | 0.3808 | 14,238.85 | sensitive |
| 9 KCl Nuclear Extract | 0.9351 | 1,330.48 | |
| 10 Total Nuclear | 0.8530 | 1,139.24 | resistant |
| 10 KCl Nuclear Extract | 2.2606 | 228.21 | |
| 11 Total Nuclear | 0.4924 | 8,757.46 | sensitive |
| 11 KCl Nuclear Extract | trans only | 950.92 | |
| 12 Total Nuclear | 1.0904 | 817.98 | resistant |
| 12 KCl Nuclear Extract | 2.0029 | 193.33 | |
| 13 Total Nuclear | 0.4367 | 8,062.12 | sensitive |
| 13 KCl Nuclear Extract | trans only | 1,667.69 | |

KCl Nuclear Extract fraction equals nuclear pellet extracted with 0.4 molar KCl followed by 200,000 G's.

Four of seven sensitive tumors had trans only in the KCl nuclear extract, in two the levels were below the limit of detectability and in one the C/T ratio was 0.9. All 5 resistant tumors had high C/T ratios. Total and KCl extracted tamoxifen was lower in resistant than in sensitive tumors.

Figure 7:
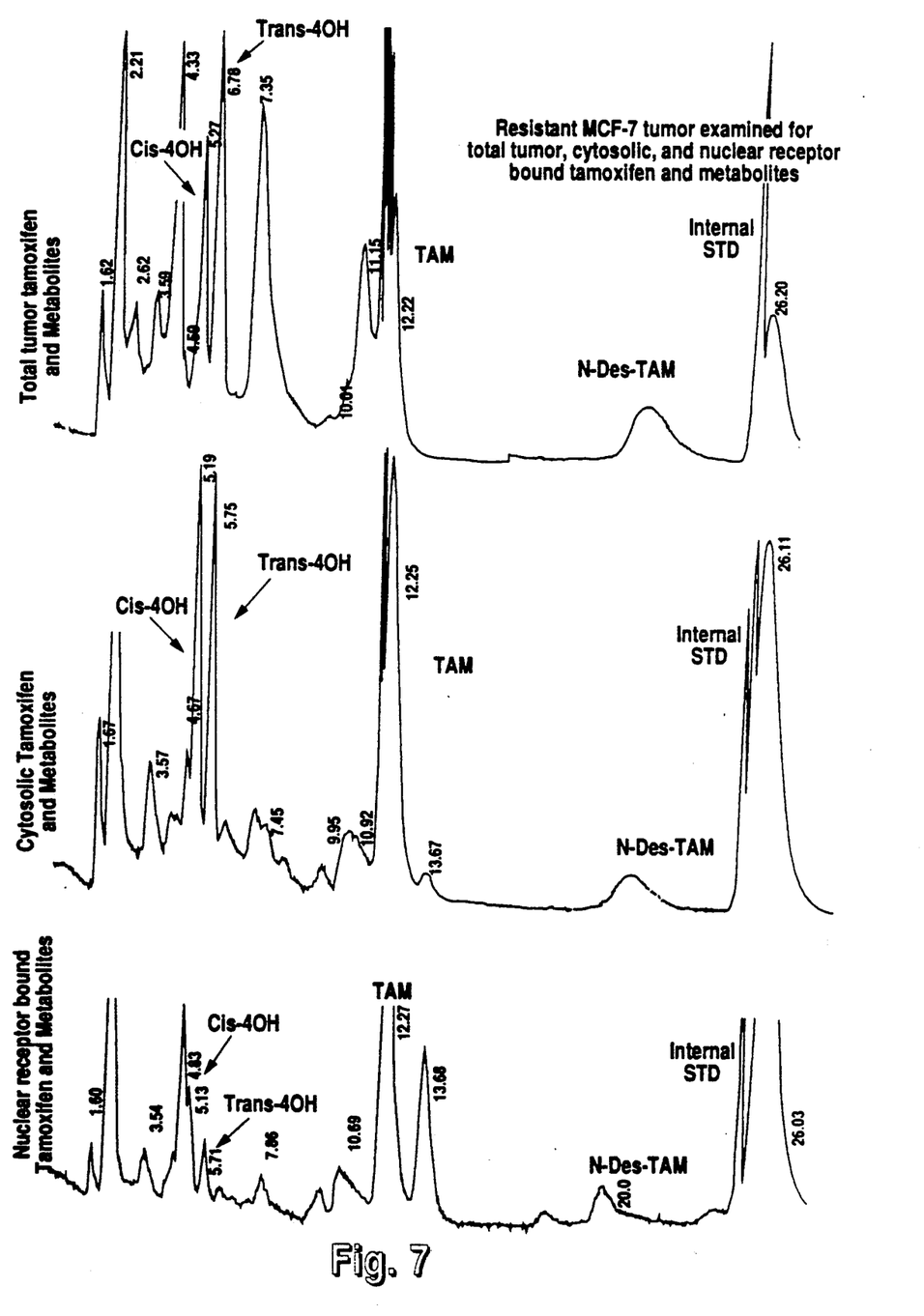
FIG. 7 shows HPLC chromatographs of a resistant tumor analyzed for total tumor tamoxifen, cytosol tamoxifen, and tamoxifen found in nuclear pellets extracted with KCl (from top to bottom, respectively).

FIG. 7 shows an HPLC chromatograph of a resistant tumor analyzed for total tumor tamoxifen, cytosol tamoxifen, and tamoxifen found in nuclear pellets extracted with KC1 (from top to bottom, respectively). This figure shows that cis 4-OH-TAM/trans-4-OH-TAM ratios are larger in the nuclear pellets extracted with KC1, which presumably represents estrogen receptor-bound drug. This observation suggests that tamoxifen resistance may be regulated by the production of the cis 4-OHTAM metabolite.

EXAMPLE 2

Human Studies

To further demonstrate that the invention is applicable in humans, several studies were carried out which demonstrate its feasibility. These include:

1) identification and measurement of tamoxifen and its metabolites in tumors isolated from tamoxifen-treated patients who are known treatment failures;
2) measurement of tamoxifen and its metabolites in serum from patients who are being treated with adjuvant doses of tamoxifen;
3) determination of cis/trans 4-OH-TAM ratios in treatment-resistant human tumors.

Table 4 shows tamoxifen concentrations and cis/trans ratios in 14 human tumor specimens from patients who were experiencing progressive disease on tamoxifen therapy. There are no tamoxifen-sensitive tumors for comparison because patients responding to treatment would not be biopsied during the responsive phase of their disease. The majority of patients whose tumors were tested had relatively high cis/trans ratios, as were noted with the MCF-7 mouse model. That is, tamoxifen-resistant human tumors have significant concentrations of the partially estrogenic metabolite, cis 4-OH-TAM.

TABLE 4

Tamoxifen/Metabolites in Total Tumor, Cytosol, and Nuclear Pellets Extracted with 0.4 molar KCl

Figure 8:
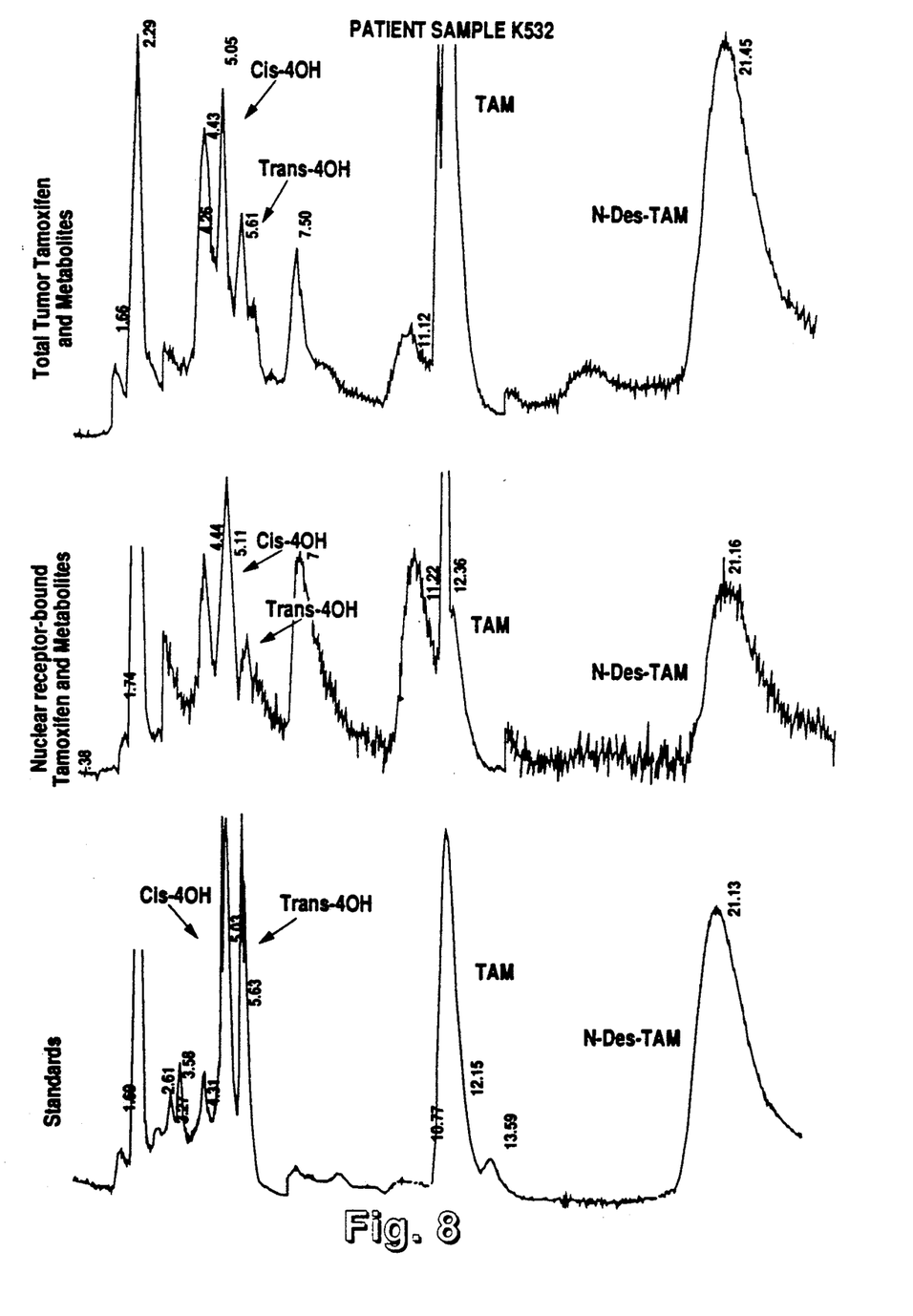
FIG. 8 shows example HPLC chromatographs demonstrating cis >trans concentrations of 4-OH-TAM extracted from tumor nuclear pellets representing patients with clinically-evident tumor resistance. These findings must be contrasted with analogous measurements for tamoxifen-sensitive tumors in the mouse model (showing trans >cis 4-OH-TAM) because sensitive tumors in human patients are not biopsied and the information is not available.

| sample patient # | | weight (mg) | Tamoxifen peak height | 4OH cis peak height | 4OH trans peak height | cis/trans ratio |
|---|---|---|---|---|---|---|
| W 131 | total | 41 | 57789 | 4587 | 3394 | 1.35 |
| | cytosol | 97 | 18504 | 1724 | 902 | 1.91 |
| | pellet | 97 | ni | 1496 | 1024 | 1.46 |
| N 184 | total | 38 | 1567 | ni | ni | 1.42 |
| | cytosol | 88 | 183 | 358 | nd | cis only |
| U 243 | total | 34 | 44604 | ni | ni | 1.23 |
| | cytosol | 77 | 9067 | 1544 | 1021 | 1.51 |
| | pellet | 77 | 5600 | ni | ni | 0.97 |
| L 281 | total | 44 | 39960 | 3324 | 12216 | 0.27 |
| | cytosol | 80 | 7369 | 1389 | 3787 | 0.37 |
| | pellet | 80 | 4795 | 1154 | 1194 | 0.97 |
| H 312 | total | 33 | 39726 | 3574 | 7749 | 0.46 |
| | cytosol | 87 | 15887 | ni | ni | 1.38 |
| | pellet | 87 | 3134 | ni | ni | 1.18 |
| G 375 | total | 49 | 17521 | 1911 | 3373 | 0.57 |
| | cytosol | 44 | 8429 | 613 | 723 | 0.85 |
| | pellet | 44 | 2523 | ni | ni | 1.29 |
| F 462 | total | 45 | 598 | nd | 3968 | trans only |
| | cytosol | 93 | 301 | 431 | 1102 | 0.39 |
| U 465 | total | 32 | 8823 | nd | 4287 | trans only |
| | total | 125 | 6672 | 640 | 1703 | 0.38 |
| | pellet | 125 | 2248 | 508 | nd | cis only |
| T 474 | total | 44 | 11987 | nd | 1481 | trans only |
| | total | 113 | 3129 | 483 | 741 | 0.65 |
| | pellet | 113 | 2737 | 311 | nd | cis only |
| Y 501 | total | 48 | 4085 | ni | ni | 1.19 |
| | cytosol | 71 | 1288 | 206 | nd | cis only |
| K 532 | total | 36 | 8850 | nd | nd | — |
| | total | 85 | 3410 | 669 | 324 | 2.06 |
| | pellet | 85 | 1131 | 305 | nd | cis only |
| I 559 | total | 65 | nd | nd | nd | — |
| | cytosol | 89 | 243 | 456 | nd | cis only |
| J 562 | total | 32 | 21965 | 3924 | nd | cis only |
| | cytosol | 64 | 6656 | 1291 | 784 | 1.48 |
| | pellet | 64 | 161 | ni | ni | 1.45 |
| J 578 | total | 36 | nd | nd | nd | — |
| | cytosol | 51 | 553 | 408 | nd | cis only | nd = not detectable
ni = no integration (ratio obtained by direct measurement)
*total = total tumor
**cytosol = total tumor except for the nucleus
***pellet = KCl nuclear extract Results of these studies show that concentrations of tamoxifen and its metabolites measured in serum, tumors, and nuclear fractions can be used to follow the response of human tumor patients. Relative increases in the cis/trans ratio and decreases in tamoxifen concentration are expected to be associated with patients whose tumors are progressing on adjuvant doses of tamoxifen. FIG. 8 shows an example of higher cis 4-OH-TAM in the nuclear pellets (extracted with 0.4 molar KC1, followed by ultracentrifugation, as in the mouse studies).

Human Serum Specimens

Figure 9:
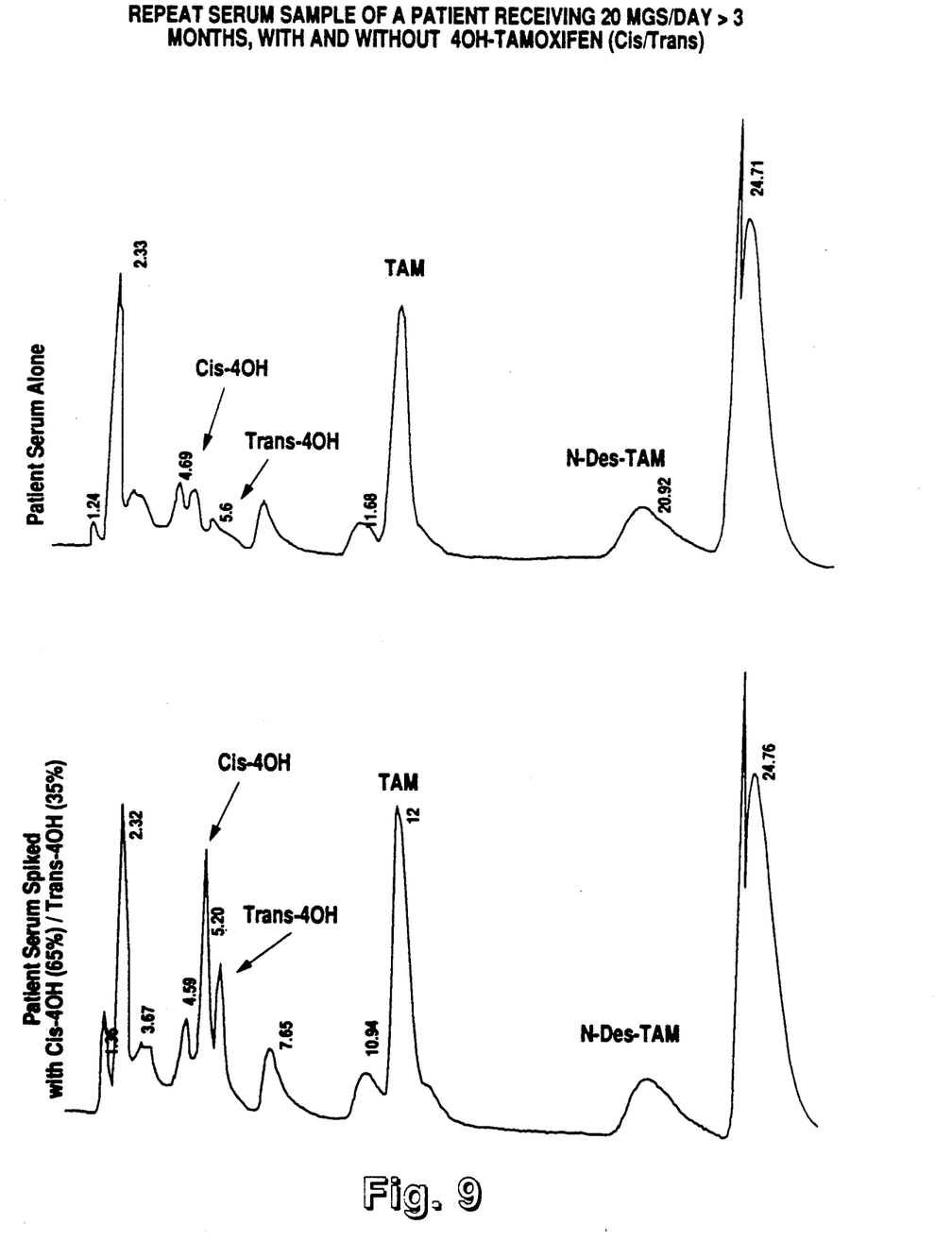
FIG. 9 shows example HPLC chromatographs demonstrating detection of tamoxifen, des-tamoxifen, and cis and trans 4-OHTAM following treatment with 20 mg tamoxifen per day. These measurements demonstrate the capability to measure tamoxifen and its metabolites in the serum.

Because directly monitoring tumor drug levels in patients requires a biopsy for each reading, it is impractical. Using a modified assay method, however, detection of tamoxifen, destamoxifen, and cis and trans 4-OH-TAM in serum is possible. FIG. 9 shows serum specimens following 20 mg daily doses of tamoxifen. Each serum specimen was spiked with cis and trans 4-OH-TAM reference standards which marked the appropriate peak in the unspiked sample. However, the relationship between plasma and tumor levels of the compounds of interest remains undetermined. Analogous results were obtained when a 160 mg tamoxifen dose was used.

Changes may be made in the construction, operation and arrangement of the various parts, elements, steps and procedures described herein without departing from the concept and scope of the invention as defined in the following claims.

What is claimed is:

1. A method for detecting in vivo development of tamoxifen-resistant breast tumors comprising:
   obtaining ratios of cis-4-hydroxy-tamosifen concentration to trans-4-hydroxy-tamoxifen concentration in tissue samples from a breast cancer patient being subjected to a course of tamoxifen treatment; and
   following said ratios during the course of tamoxifen treatment to determine onset of treatment resistance as characterized by an increase in the ratio of cis-4-hydroxy-tamoxifen concentration to trans-4-hydroxy-tamoxifen concentration.

2. The method according to claim 1 wherein said tissue is breast tumor.

3. The method according to claim 1 wherein said tissue is blood.

4. A method for detecting in vivo development of tamoxifen-resistant breast tumors comprising:
   obtaining breast tumor tamoxifen concentration in a patient during a course of tamoxifen treatment; and
   following said concentration during the course of tamoxifen treatment to determine onset of treatment resistance as characterized by a decrease in said tamoxifen concentration.

5. A method for detecting in vivo development of tamoxifen-resistant breast tumors comprising:
   obtaining breast tumor tamoxifen concentrations and tissue ratios of cis-4-hydroxy-tamoxifen concentration to trans-4-hydroxy-tamoxifen concentration in a patient being subjected to a course of tamoxifen treatment; and
   following said tamoxifen concentrations and ratios during the course of tamoxifen treatment to determine onset of treatment resistance as characterized by a decrease in tamoxifen concentration and an increase in the ratio of cis-4-hydroxy-tamoxifen concentration to trans-4-hydroxy-tamoxifen concentration.

6. The method according to claim 5 wherein said tissue is breast tumor.

7. The method according to claim 5 wherein said tissue is blood.

8. A method for detecting in vivo development of resistance in breast tumors to treatment by a triphenylethylene estrogen comprising:
   obtaining concentration ratios tissue of cis to trans forms of triphenylethylene antiestrogen in a patient being subjected to a course of treatment with a triphenylethylene antiestrogen; and
   following said ratios during the course of treatment to determine onset of treatment resistance as characterized by an increase in the ratio of concentration of cis to trans forms of said triphenylethylene antiestrogen.

9. The method according to claim 8 wherein said tissue is breast tumor.

10. The method according to claim 8 wherein said tissue is blood.

11. The method according to claim 1, 5 or 8 wherein said obtaining step comprises photoactivation of a tissue sample extract.

12. The method of claim 11 wherein the photoactivation involves irradiation with ultraviolet light.

13. The method of claim 1, 5 or 8 wherein the obtaining step comprises high performance liquid chromatography.

14. A method for detecting in vivo development of tamoxifen-resistant breast tumors in a breast cancer patient being subjected to a course of tamoxifen treatment, the method comprising:
   obtaining tissue ratios of cis-4-hydroxy-tamoxifen concentration to trans-4-hydroxy-tamoxifen concentration in said patient; and
   following said ratios during the course of tamoxifen treatment to determine onset of treatment resistance as characterized by an increase in the ratio of cis-4-hydroxy-tamoxifen concentration to trans-4-hydroxy-tamoxifen concentration.

* * * * *

UNITED STATES PATENT AND TRADEMARK OFFICE
CERTIFICATE OF CORRECTION

PATENT NO. : 5,119,827

DATED : June 9, 1992

INVENTOR(S) : C. Kent Osborne, et al

It is certified that error appears in the above-identified patent and that said Letters Patent is hereby corrected as shown below:

On the title page, Item [75]: delete Inventors "C. Kent Osborne, San Antonio, Tex,; Michael W. De Gregorio, Hamden, Conn." and insert —C. Kent Osborne, San Antonio, Tex.; Michael W. DeGregorio, San Antonio, Tex.—

Col. 9 line 7, delete "in vivo" and insert —in vivo—.
line 9, delete "cis-4-hydroxy-tamosifen" and insert —cis-4-hydroxy-tamoxifen—.

line 23, delete "in vivo" and insert —in vivo—.
line 25, delete "concentration" and insert —concentrations—.
line 31, delete "in vivo" and insert — in vivo—.

Col. 10 line 7, delete "in vivo" and insert —in vivo—.
line 31, delete "in vivo" and insert —in vivo—.

Signed and Sealed this

Tenth Day of August, 1993

Attest:

MICHAEL K. KIRK

Attesting Officer

Acting Commissioner of Patents and Trademarks